United States Patent [19]

DeRoche et al.

[11] Patent Number: 4,548,976
[45] Date of Patent: Oct. 22, 1985

[54] BIS-(NORBORNYL OR SUBSTITUTED NORBORNYL) DERIVATIVES OF A PHENOL OR A PHENYLAMINE, PROCESS FOR THEIR PREPARATION AND COMPOSITIONS CONTAINING SAME

[75] Inventors: Pierre DeRoche, Horgen, Switzerland; Neil V. Kirby, Wisbech, England

[73] Assignee: The Dow Chemical Company, Midland, Mich.

[21] Appl. No.: 611,807

[22] Filed: May 18, 1984

[51] Int. Cl.$^4$ .......................... C08K 5/13; C08K 5/18; C08K 5/36; C07C 39/11
[52] U.S. Cl. .................................. 524/249; 525/290; 525/244; 524/324; 564/430; 564/433; 564/434; 568/718; 568/719; 568/721; 568/25
[58] Field of Search ............... 568/718, 721, 722, 719, 568/727, 729; 524/324, 249; 564/430, 433, 434; 525/290, 244; 526/244

[56] References Cited

U.S. PATENT DOCUMENTS

| | | | |
|---|---|---|---|
| 3,068,198 | 12/1962 | Haines et al. | 568/727 |
| 4,219,052 | 3/1982 | Styskin et al. | 568/727 |

FOREIGN PATENT DOCUMENTS

| | | | |
|---|---|---|---|
| 207577 | 12/1955 | Australia | 568/721 |
| 1051864 | 3/1959 | Fed. Rep. of Germany | 568/727 |
| 728290 | 4/1955 | United Kingdom | 525/290 |
| 728291 | 4/1955 | United Kingdom | 525/290 |
| 732928 | 6/1955 | United Kingdom | 568/729 |
| 457685 | 3/1975 | U.S.S.R. | 568/721 |

OTHER PUBLICATIONS

Wegler et al., "Chem. Abstracts", pp. 1939–1940, (1950), vol. 44.
Hultzsch, "J. Prakt. Chem.", 159, pp. 155–179, (1941).
Chem. Abstracts, pp. 4059–4060, (1943), vol. 37.

Primary Examiner—Werren B. Lone

[57] ABSTRACT

Bis-(norbornyl or substituted norbornyl) derivatives of a phenol or phenylamine of the following formula:

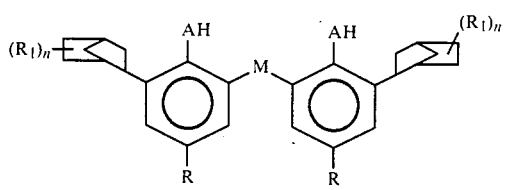

wherein each A is O or NH; M is a bivalent radical such as the residue of an aldehyde, ammonia, water or $H_2S$; each R is a hydrocarbyl or an inertly substituted hydrocarbyl group; each $R_1$ is independently a hydrocarbyl or an inertly substituted hydrocarbyl group and each n is independently an integer from 0 to 3 are useful as antioxidants for a variety of materials including latex compositions for preparing latex foam backed carpets.

6 Claims, No Drawings

BIS-(NORBORNYL OR SUBSTITUTED NORBORNYL) DERIVATIVES OF A PHENOL OR A PHENYLAMINE, PROCESS FOR THEIR PREPARATION AND COMPOSITIONS CONTAINING SAME

BACKGROUND OF THE INVENTION

The present invention relates to hindered phenyl compounds, particularly bis-(norbornyl or substituted norbornyl) derivatives of a phenol or a phenylamine, a process for their preparation and compositions containing the bis-(norbornyl or substituted norbornyl) derivatives.

Oxidation of polymeric compositions (e.g., the formation of conjugated double heads in a polymer matrix having carbon to carbon double bonds) is known to deleteriously effect the physical properties of the composition. For example, the tensile strength and physical integrity of various polymeric films or coatings are significantly degraded upon excessive oxidation.

Certain phenols substituted in the 2 and 6 positions (commonly referred to as "hindered phenols") and various 2,6-substituted phenylamines can be employed as antioxidants to protect polymeric materials from oxidation. For example, a di-butyl-para-cresol is widely employed as an antioxidant in a variety of compositions. Unfortunately, large amounts of this material and other hindered phenols or phenylamines having a similarly low molecular weight are generally required to impart the desired antioxidant effect to the compositions. In addition, di-butyl-para-cresol and the like possess relatively high volatilities which make them less practical, from a commercial standpoint, for many applications.

British Patent Specification Nos. 728,290 and 728,291 disclose bis(2-hydroxy-3-α-alkylcycloalkyl-5-methylphenyl)methanes wherein the cycloalkyl groups are cyclopentyl, methylcyclopentyl, cyclohexyl or methylcyclohexyl as antioxidants. The disclosed compounds melt at relatively high temperatures, e.g., about 120° C. and above. Due to these high melting points, the disclosed antioxidants are not effectively employed in various applications. For example, in the preparation of latex foam backed carpets, a mechanical froth of a polymeric latex composition, a filler and a cross-linking agent for the polymer is deposited on the back of the carpet and subsequently dried and cured at elevated temperatures. Although temperatures of up to and exceeding 140° C. are employed to dry and cure the polymer, due to the evaporation of the water and the heating time required, the latex compositions are generally not exposed, for the required time period, to temperatures sufficiently high to melt the antioxidant and to uniformly distribute it through the latex composition. This results in poorer resistance of the foam backed carpet to oxidation.

An alternative hindered phenol is disclosed as bis(2-hydroxy-3-butyl-5-ethylphenyl)methane. This compound also melts at a relatively high temperature and, upon melting, forms a relatively volatile liquid.

In view of the deficiencies of the antioxidants known to the prior art, it is highly desirable to prepare an effective antioxidant having a relatively low melting ranging from 90° to 120° C. and a desired low volatility.

SUMMARY OF THE INVENTION

In one aspect, the present invention is a novel compound, the novel compound being a bis-(norbornyl or substituted norbornyl) derivative of a phenol or a phenylamine having the following formula:

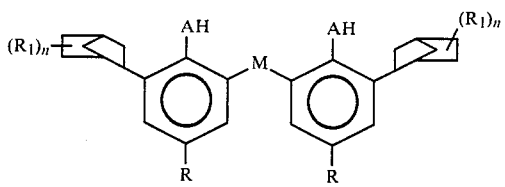

wherein each A is independently O or NH; M is a bivalent radical such as the residue of an aldehyde, ammonia, water or $H_2S$; each R is independently a hydrocarbyl or substituted hydrocarbyl group, each $R_1$ is independently a hydrocarbyl or a substituted hydrocarbyl group and each n is independently from 0 to 3, preferably 0 or an integer from 1 to 3. Preferably in the designated formula, A is oxygen, M is the residue of an aldehyde such as formaldehyde or a formaldehyde-yielding compound such as paraformaldehyde and the like (i.e., $-CH_2-$), R is an alkyl or an inertly substituted alkyl group, particularly methyl or ethyl, each $R_1$ if any, is an alkyl, preferably methyl and each n is independently 0 or 1. Most preferably, each A is 0, M is $-CH_2-$, each R is methyl and each n is 0.

As indicated, reference herein to phenyl compounds or derivatives and hindered phenyl compounds or derivatives is meant to connote compounds or derivatives or a phenol or a phenylamine (i.e., an aromatic amine such as aniline). In addition, reference herein to norbornene or norbornyl compounds is meant to include substituted norbornene or norbornyl compounds such as 2-methyl-5-norbornene. The substituents present on any substituted hydrocarbyl groups should generally be such as to be inert to the formation reactions, and the oxidation reactions it is desired to inhibit.

Surprisingly, the described norbornyl derivatives melt at unexpectedly low temperatures when compared to the bis-(hindered phenyl) compounds known in the prior art of the same or similar molecular weight. For example, the most preferred bis-(norbornyl or substituted norbornyl phenyl) derivative (i.e., bis-(2-hydroxy-3-norbornyl phenyl-5-methyl)methane) melts at a temperature from 100° to 104° C. Therefore, when employed as antioxidants, the compounds of the present invention can more uniformly be dispersed throughout the compositions to be protected against oxidation even though the compositions are exposed to relatively low temperatures such as encountered in the preparation of latex foam backed carpets. In addition, the bis-(norbornyl or substituted norbornyl phenyl) derivatives of the present invention exhibit lower volatilities.

DETAILED DESCRIPTION OF THE INVENTION

The hindered phenyl compounds of the present invention are usefully employed as antioxidants in a variety of materials such as oils, fats and waxes which tend to deteriorate in the presence of oxygen and in polymers, particularly natural and synthetic rubbers and, in another aspect, the present invention is a composition having an improved resistance to oxidation, said composition comprising a material susceptible to oxidation and an amount of the bis-(norbornyl or substituted norbornyl phenyl) derivative sufficient to improve the resistance of the material to oxidation. In a preferred embodiment, the composition is a polymer latex composition useful in the preparation of foam backed carpets containing an amount of the bis-(norbornyl or substituted norbornyl phenyl) derivative sufficient to improve the resistance of the polymer to oxidation after its application to a carpet backing.

The bis-(norbornyl or substituted norbornyl phenyl) derivative of the present invention are advantageously prepared using two process steps. The first step comprises a substitution reaction wherein a 4-substituted phenyl compound is reacted with norbornene to form the 2-norbornyl derivative of the phenyl compound. The second step comprises a coupling reaction wherein the norbornyl substituted phenyl compound is reacted with a coupling agent which chemically combines or couples two molecules of the norbornyl substituted phenyl compound to form the desired bis-(norbornyl phenyl) derivatives.

The substitution reaction of the 4-substituted phenyl compound with the norbornene is advantageously conducted in the presence of a suitable catalyst, preferably a Friedel-Crafts catalyst and at conditions sufficient to form a 2-norbornyl, 4-substituted phenyl compound. The amounts of the phenyl compound and norbornene most advantageously employed in the preparation of the norbornyl substituted phenyl compound are dependent on various factors, including the specific catalyst and the reaction conditions employed. In general, the phenyl compound is employed in a stoichiometric excess amount, preferably an amount sufficiently in excess to insure monosubstitution (as opposed to di or greater amounts of substitution) of the norbornene per molecule of the 4-substituted phenyl compound. In general, from about 2 to 5 moles of the 4-substituted phenyl compound are preferably employed for each mole of the norbornene employed.

The 4-substituted phenyl compounds useful in the preparation of the norbornyl substituted phenyl compound of the present invention are of the formula:

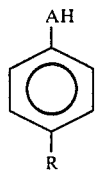

wherein A is NH or oxygen, preferably oxygen, and R is a hydrocarbyl or inertly substituted hydrocarbyl which permits the addition of the norbornene in the ortho position with respect to the hydroxy or amino group. Preferably, R is an alkyl group. Most preferably, R is methyl.

Any catalyst capable of catalyzing the substitution reaction is suitably employed in the practice of the present invention, with Friedel-Crafts catalysts being, in general, preferred. Representative Friedel-Craft catalysts are disclosed in *Friedel-Crafts Chemistry* by G. A. Olah, published in 1973 by John Wiley and Sons, New York. Of the Friedel-Craft catalysts, those which are generally advantageously employed in conducting the reaction include the proton acids such as sulfuric acid, hydrochloric acid and phosphoric acid; the acidic oxides such as $HClO_4$; and the acidic metal halides such as boron trifluoride ($BF_3$), boron trichloride ($BCl_3$), aluminum trichloride ($AlCl_3$), aluminum tribromide ($AlBr_3$), zinc dichloride ($ZnCl_2$), tin tetrachloride ($SnCl_4$), antimony trichloride ($SbCl_3$) and the like. The preferred catalysts are the metal halides, with $BF_3$ and $AlCl_3$ being most preferred.

The catalyst is advantageously employed in an amount sufficient to catalyze the substitution reaction. Typically, such amounts will vary depending on the type and concentration of the reactants and the reaction conditions employed. Generally, the catalyst is employed in amounts from 1 to 50, preferably from 5 to 20, mole percent based on the moles of the norbornene employed.

Although the substitution reaction can be conducted by dissolving or dispersing the reactants in a suitable, inert solvent such as nitro- or chlorobenzene, the reaction is more advantageously conducted neat, i.e., no additional solvent being employed.

In conducting the substitution reaction, although the order of addition of the catalyst and reactants is not particularly critical, the norbornene is advantageously added to a mixture of the 4-substituted phenyl compound and catalyst. The addition of the norbornene to the reaction mixture is advantageously conducted in a continuous manner. Although less preferred, intermittent addition of the norbornene, i.e., addition in two or more increments, can be employed. During this addition and the ensuing reaction, the reaction mixture is maintained at the desired temperatures while the mixture is advantageously agitated to maintain an essentially homogeneous mixture of the reactants. The substitution reaction is advantageously conducted at temperatures ranging from 50° to 90° C. Generally, reaction temperatures ranging from 70° to 80° C. are preferred. In general, reaction pressure is not critical, with pressures between 0 and 25 atmospheres advantageously being employed.

At the specified temperatures, the substitution reaction generally requires a reaction time of from one to three hours, including the addition of the norbornene to the reaction mixture.

Following the substitution reaction, the reaction mixture is cooled to ambient temperatures, e.g., from 18° to 25° C., and the 2-norbornyl-4-R substituted phenyl compound recovered. In general, such recovery is advantageously conducted by neutralizing the norbornyl phenyl derivative, extracting the neutralized reaction product using conventional solvent-solvent extraction techniques and subsequently separating the extracted, neutralized product from the organic phase such as by evaporating the solvent from the reaction product.

The bis-(norbornyl phenyl) derivative is then prepared by contacting the norbornyl phenyl derivative with a suitable coupling agent in the presence of an acid catalyst and at conditions sufficient to form the desired bis-(norbornyl phenyl) derivative.

Any compound capable of forming a chemical bond between (i.e., coupling) two of the norbornyl substituted phenyl molecules is suitably employed herein as the coupling agent. The coupling agent can be an aldehyde such as formaldehyde (advantageously in the form of an aqueous solution such as formalin), a formaldehyde yielding material such as paraformaldehyde, acetaldehyde, furfural, butyraldehyde and the like; water; hydrogen sulfide or ammonia. Preferably, the coupling agent is an aldehyde. Most preferably, the coupling agent is formaldehyde or a formaldehyde generating material such as paraformaldehyde.

In general, the coupling agent is employed in a stoichiometric excess amount, i.e., an amount in excess of that amount required to couple all the norbornyl phenyl derivative employed. Specifically, from 0.5 to 1, more preferably from 0.6 to 0.8 moles of the coupling compound are employed per mole of the norbornyl phenyl derivative.

Acids employed as catalysts in the coupling reaction are Lewis acids which are capable of catalyzing the reaction. In general, the acids useful as catalysts have a $pK_a$ of less than 1.5 when measured at 25° C. Representatives of such acids are the mineral acids such as phosphoric acid, sulfuric acid, hydrochloric acid, alkyl or aryl sulfonic or phosphoric acids, e.g., p-toluene sulfonic acid; trichloro(or fluoro) acetic acid; and mixtures thereof. The preferred acid for use as a catalyst is hydrochloric acid.

The acid catalyst is advantageously employed in an amount sufficient to catalyze the coupling reaction. Such amounts will vary depending on the type and concentration of the reactants (i.e., the specific norbornyl substituted phenyl derivative and coupling agent used) and the reaction conditions employed. Generally, the acid catalyst is employed in amounts from 0.01 to 1, preferably from 0.05 to 0.25, weight parts per weight part of the norbornyl substituted phenyl derivative.

In conducting the coupling reaction, the norbornyl substituted phenyl derivative, the acid catalyst and the coupling agent are advantageously mixed and heated to the desired reaction temperature while agitating the reaction mixture to maintain an essentially homogeneous mixture of the reactants. In general, the reaction is advantageously conducted without the addition of reaction diluents.

The coupling reaction is advantageously conducted at elevated temperatures from 80 to the temperature at which the reaction mixture boils. Preferably, the coupling reaction is conducted at temperatures from 90° to 110° C. At these temperatures, the coupling reaction generally requires a reaction time of at least 0.2, advantageously at least 0.5 hours. Preferably, reaction times from 0.5 to 1.5 hours are employed.

Following completion of the coupling reaction, the reaction mixture is cooled and the bis-(norbornyl phenyl) derivative recovered. In general, such recovery is easily effected by washing the reaction product with water and crystallizing the reaction product from petroleum spirits.

The resulting bis-(norbornyl phenyl) derivative can subsequently be employed as an antioxidant within a variety of compositions including synthetic or natural rubbers, plastics, polymeric latex compositions and the like without further modification. In a preferred embodiment, the bis-(norbornyl phenyl) derivatives are employed as an antioxidant in a latex formulation useful in the preparation of latex foam backed carpets. Such latexes are well known in the art and reference is made thereto for the purposes of this invention. Illustrative of said latex composition and its method of use is disclosed by British Pat. No. 1,023,202.

In general, the latex formulations useful in the preparation of latex foam backed carpets generally comprise an aqueous dispersion of colloidal sized, polymer particles (so-called "latex") of a copolymer of styrene and butadiene and, optionally, other copolymerizable monomers, a filler such as calcium carbonate; a cross-linking agent for the polymer such as a melamine-formaldehyde resin and optionally, other adjuncts such as emulsifiers, thickeners, stabilizers and the like. In general, the preferred latex compositions comprise, for each 100 parts (dry) of polymer, from 100 to 250 parts of the filler and from 2 to 20 parts of the cross-linking agent.

In the latex formulations for preparing latex foam backed carpets, the bis-(norbornyl phenyl) derivative is advantageously employed in an amount from 0.1 to 5, preferably from 0.2 to 2, weight percent based on the total weight of the polymer (dry) in the latex composition.

In preparing the latex formulations containing the bis-(norbornyl phenyl) derivative as an antioxidant, the bis-(norbornyl phenyl) derivative is advantageously added to the latex, which may or may not contain the filler, curing agent and other optionally employed adjuncts, as a dispersion in water. Advantageously, the aqueous dispersion comprises from 30 to 70 preferably from 40 to 60, weight percent of the bis-(norbornyl phenyl) derivative. To aid in forming a stable, aqueous dispersion, the dispersion, in addition to the derivative, advantageously contains a dispersing agent. The dispersing agent is suitably a surfactant compatible with the bis-(norbornyl phenyl) derivative and the latex compositions. The surfactants can be anionic, cationic, nonionic or amphoteric depending on the specific latex composition employed. Representative surfactants are the alkali metal salts of long chain fatty acids, e.g., potassium oleate; the aryl sulfonates, e.g., naphthalene sulfonate and the like. Although the amount of the dispersing aid most advantageously employed will be dependent on the specific dispersing aid and bis-(norbornyl phenyl) derivative, the dispersing aid is generally advantageously employed in an amount from 0.2 to 10 weight percent based on the weight of the dispersion.

In practice, the latex formulation containing the bis-(norbornyl phenyl) derivative is applied to the back of a carpet, dried and cured using techniques well-known in the art for the preparation of latex foam backed carpets. In general, such techniques include mechanically frothing the latex formulation with air and subsequently applying the latex to the back of the carpet by means of an ejector nozzle. The latex is then dried and cured at elevated temperatures. In a preferred method, a split-zone oven having infrared pre-heaters is used to dry and cure the latex. In general, this operation is conducted at temperatures from 80° to 190° C., more generally from 100° to 160° C.

The following examples are presented to illustrate the present invention and should not be construed to limit its scope. All percentages and parts in the examples are by weight unless otherwise indicated.

EXAMPLE 1

A. Preparation of 4-methyl-2-norbornyl phenol

To a suitably sized flask equipped with a thermometer, stirrer, reflux means and heating and cooling means is added 90 grams (g) of p-cresol (0.83 mole) and 3 milliliters (mls) of a boron trifluoride diethyl etherate catalyst. This mixture is heated, with agitation, in a nitrogen atmosphere to 65° C. After the reaction mixture has reached this temperature, 25.73 g (0.27 mole) of norbornene is added dropwise to the flask. During this addition, the reaction temperature is maintained in the range from 65°–75° C. and the reaction mixture is continuously agitated to assure homogeneous mixing of the reactants. The addition of the norbornene takes approximately one hour. After complete addition of the norbornene, the resulting mixture is maintained at 75° C.

for one hour. The mixture is then cooled to ambient temperatures.

To the cooled mixture is added an aqueous solution of sodium carbonate consisting of 18 g of sodium carbonate dissolved in 60 mls of water. The resulting mixture is heated under reflux for 1 hour. It is then cooled to ambient temperatures and the oil phase separated and washed with a solution of 30 g of sodium hydroxide (0.75 mole) and 300 mls of water. The aqueous phase is then separated using conventional techniques. The remaining organic phase is then washed with 100 mls of water, dried over anhydrous sodium sulphate and the solvent evaporated under reduced pressures to give a gold viscous oil which, when purified by distillation, gives 30.54 g of a 4-methyl-2-norbornyl phenol. The 4-methyl-2-norbornyl phenol has a boiling point of approximately 120° C. at 0.2 mm Hg.

B. Preparation of bis-(2-hydroxy-3-norbornyl-5-methylphenyl)methane

To a suitably sized flask equipped with thermometer, stirrer and heating and cooling means is added 40 g (0.198 mole) of the 4-methyl-2-norbornyl phenol, 3 g of paraformaldehyde (0.1 mole) and 4.1 g of a hydrochloric acid having a specific gravity of 1.18. This mixture is heated, with agitation, to a temperature between 100° to 110° C. It is maintained at this elevated temperature for one hour and then cooled to ambient temperatures. The resultant pale green gum is crystallized from petroleum spirit (40°–60° C.) to give 19.5 g of a product primarily consisting of the desired bis-(2-hydroxy-3-norbornyl-5-methylphenyl)methane. This product had a melting point of between 100°. When further purified, the melting point is found to be about 103° C.

C. Preparation of a latex formulation containing the bis-(norbornyl-phenyl) antioxidant A conventional latex formulation for use in producing latex foam backed carpets is prepared by mixing 175 parts of an aqueous dispersion comprising 57 percent of colloidal sized polymer particles of a copolymer of styrene and butadiene, 150 parts of a calcium carbonate filler and 7.5 parts of melamine formaldehyde resin used as a cross-linker for the styrene-butadiene copolymer. The formation also contains added, anionic surfactant; a cellulosic thickener and stabilizers. To the resulting latex formulation is added an aqueous dispersion containing 50 percent of the bis-(norbornyl phenyl) derivative and 3 percent of naphthalene sulfonate as a dispersion aid. The latex formulation containing the bis-(norbornyl phenol) derivative as an antioxidant is mechanically frothed with air and then sprayed through a nozzle to the back of a carpet. The carpet is then fed through an oven containing infrared pre-heaters to form a skin on the latex. Subsequently, the latex/carpet combination is treated in a split zone oven heated to temperatures of about 140° C.

After preparation, the foam backed carpets are cut in a dumb bell shape and subjected to accelerating aging conditions. After 8 days in an oxidizing atmosphere, the carpet backed with the latex containing the bis-(norbornyl phenyl) antioxidant remains flexible and exhibits a relatively high percentage of its original elastomeric properties which include elongation and tensile strength.

COMPARATIVE EXAMPLE 1

Bis-(2-hydroxy-3-cyclohexyl-5-methylphenyl)methane is prepared by the techniques described in British Patent Specification No. 728,290. The resulting product has a melting point of 130°–132° C.

A latex formulation identical to that of Example 1 is prepared except that the bis-(2-hydroxy-3-cyclohexyl-5-methylphenyl)methane is used in place of the bis-(norbornyl phenyl) derivative. It is applied to a carpet backing in the manner described in Example 1 and dumb bell shaped samples are prepared therefrom. The high melting temperature of the bis-(2-hydroxy-3-cyclohexyl-5-methylphenyl)methane is believed to hinder the ability of said compound to become as uniformly dispersed throughout the carpet backing during processing.

After eight days of accelerated aging, the aged carpet samples are more brittle and significantly more of the original elastomeric properties of the latex backed carpet samples is lost.

COMPARATIVE EXAMPLE 2

A latex formulation identical to that of Example 1 except prepared using a bis-(2-hydroxy-3-butyl-5-methylphenyl)methane. The bis-(2-hydroxy-3-butyl-5-methylphenyl)methane has a melting point between 125° and 130° C. which limits its ability to be uniformly dispersed throughout the latex formulation during processing. The foam backed carpets prepared therefrom exhibit a similar reduced performance as exhibited by the latex formulation prepared in Comparative Example 1.

Similar reduced antioxidant effects are found using a bis-(2-hydroxy-3-tertbutyl-5-ethylphenyl)methane.

We claim:

1. A bis-(norbornyl or substituted norbornyl) derivative of a phenol or a phenylamine of the formula:

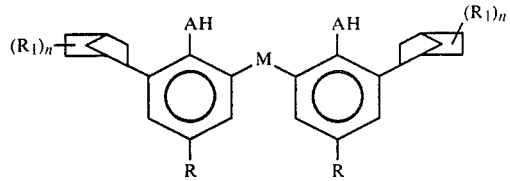

wherein each A is independently O or NH; M is a bivalent radical; each R is independently a hydrocarbyl or substituted hydrocarbyl group which permits the addition of the norbornene at the ortho position with respect to AH, each $R_1$ is independently a hydrocarbyl or a substituted hydrocarbyl group and each n is independently from 0 to 3.

2. The bis-(norbornyl phenyl) derivative as claimed in claim 1 wherein A is oxygen; M is —$CH_2$—; R is an alkyl or an inertly substituted alkyl group; $R_1$, if present, is an alkyl group and each n is independently 0 or 1.

3. The bis-(norbornyl phenyl) derivative as claimed in claim 2 wherein each A is oxygen, M is $CH_2$, each R is $CH_3$ or $C_2H_5$, and each n equals 0.

4. A composition having an improved resistance to oxidation, said composition comprising a polymeric material susceptible to oxidation and an amount of a bis-(norbornyl or substituted norbornyl) derivative as claimed in any one of claims 1 to 3 sufficient to improve the resistance of the material to oxidation.

5. A latex composition comprising an aqueous dispersion of colloidal sized, polymer particles of a copolymer of styrene and a butadiene; a filler; a cross-linking agent for the polymer and an amount of a bis-(norbornyl phenyl) derivative as claimed in any one of claims 1 to 3 sufficient to improve the resistance of the composition to oxidation after its application to carpet backing.

6. The latex composition of claim 5 which additionally includes other copolymerizable monomers.

* * * * *

UNITED STATES PATENT AND TRADEMARK OFFICE
CERTIFICATE OF CORRECTION

PATENT NO. : 4,548,976

DATED : October 22, 1985

INVENTOR(S) : Pierre DeRoche; Neil V. Kirby

It is certified that error appears in the above-identified patent and that said Letters Patent is hereby corrected as shown below:

Column 1, line 16, "heads" should read --bonds--.

Column 7, line 32, "between" should read --about--; line 44, "formation" should read --formulation--.

Signed and Sealed this

Twenty-ninth Day of July 1986

[SEAL]

Attest:

DONALD J. QUIGG

Attesting Officer

Commissioner of Patents and Trademarks